(12) United States Patent
Csernatoni

(10) Patent No.: US 9,962,211 B2
(45) Date of Patent: May 8, 2018

(54) HANDHELD INSTRUMENT ASSEMBLY

(71) Applicant: Amendia, Inc., Marietta, GA (US)

(72) Inventor: Zsolt Csernatoni, Woodstock, GA (US)

(73) Assignee: Amendia, Inc., Marietta, GA (US)

( * ) Notice: Subject to any disclaimer, the term of this patent is extended or adjusted under 35 U.S.C. 154(b) by 0 days. days.

(21) Appl. No.: 14/958,216

(22) Filed: Dec. 3, 2015

(65) Prior Publication Data

US 2017/0156751 A1 Jun. 8, 2017

(51) Int. Cl.
*A61B 17/88* (2006.01)
*A61B 17/34* (2006.01)
*A61B 17/00* (2006.01)

(52) U.S. Cl.
CPC ...... *A61B 17/8819* (2013.01); *A61B 17/3403* (2013.01); *A61B 17/3472* (2013.01); *A61B 17/8802* (2013.01); *A61B 17/8825* (2013.01); *A61B 2017/0046* (2013.01)

(58) Field of Classification Search
CPC ............ A61B 17/8802; A61B 17/8819; A61B 17/8825; A61B 17/1703; A61B 17/3403; A61B 17/3405; A61B 17/3472; A61B 17/3468; A61B 2017/0046; A61B 2017/347; A61B 10/025; A61B 2019/5238; Y10T 16/469
USPC ............ 81/489, 177.1, 177.2, 177.85, 177.5; 30/356; 7/167; 173/90, 170, 29
See application file for complete search history.

(56) References Cited

U.S. PATENT DOCUMENTS

| | | | |
|---|---|---|---|
| 4,262,676 A | 4/1981 | Jamshidi | |
| 5,257,632 A | 11/1993 | Turkel et al. | |
| 5,368,046 A | 11/1994 | Scarfone et al. | |
| 5,372,583 A * | 12/1994 | Roberts | A61M 25/06 600/567 |
| 5,385,151 A | 1/1995 | Scarfone et al. | |
| 5,461,950 A * | 10/1995 | Iwinski | B25B 13/463 81/61 |
| 5,595,186 A * | 1/1997 | Rubinstein | A61B 10/025 600/564 |
| 5,758,655 A | 6/1998 | Como et al. | |

(Continued)

FOREIGN PATENT DOCUMENTS

WO WO 2007039036 A1 * 4/2007 ............. A61B 17/34

OTHER PUBLICATIONS

Machine translation of the description of Ryang et al. WO2007039036.*

*Primary Examiner* — Matthew Lawson
*Assistant Examiner* — Amy Sipp
(74) *Attorney, Agent, or Firm* — David L. King

(57) ABSTRACT

An improved handheld instrument assembly for penetrating into a patient's spine, the instrument assembly has a needle, an outer sleeve, and a removable handle. The needle has a shaft with a bone penetrating tip at a distal end and an enlarged head rotationally fixed to the needle shaft at a proximal end. The outer sleeve is for receiving the needle. The removable handle is configured to removably attach to and engage the handle attachment from the distal side or the proximal side at the discretion of a surgeon. The removable handle has a "T" shaped body. The removable handle has a slotted opening on a frontal side, the slotted opening being sized to pass over the outer sleeve between the distal end and the handle attachment when the needle is inserted into the patient.

1 Claim, 8 Drawing Sheets

(56) References Cited

U.S. PATENT DOCUMENTS

| | | |
|---|---|---|
| 6,554,778 B1 | 4/2003 | Fleming |
| 7,331,930 B2 * | 2/2008 | Faciszewski ........ A61B 10/025 600/567 |
| 7,399,306 B2 | 7/2008 | Reiley et al. |
| 8,348,894 B2 | 1/2013 | Swisher et al. |
| 8,784,330 B1 | 7/2014 | Scholl et al. |
| 2003/0004528 A1 * | 1/2003 | Ishikawa ............ A61B 17/3415 606/169 |
| 2003/0083592 A1 * | 5/2003 | Faciszewski ........ A61B 10/025 600/564 |
| 2008/0045965 A1 * | 2/2008 | Miller .................. A61B 10/025 606/80 |
| 2010/0114110 A1 * | 5/2010 | Taft ...................... A61B 17/025 606/108 |
| 2011/0093024 A1 * | 4/2011 | Layne ................ A61B 17/1671 606/86 R |
| 2013/0226210 A1 * | 8/2013 | Murphy ............. A61B 17/3403 606/185 |
| 2015/0223786 A1 * | 8/2015 | Morgan ............... A61B 10/025 600/567 |
| 2016/0045241 A1 * | 2/2016 | Boboltz ............. A61B 17/8819 606/93 |

\* cited by examiner

HANDHELD INSTRUMENT ASSEMBLY

TECHNICAL FIELD

The present invention relates to a bone penetrating needle assembly device with a removable handle for improved imaging.

BACKGROUND OF THE INVENTION

There are numerous devices using a needle or trocar with a sharpened bone penetrating tip. Most are two part devices having a needle and an outer sleeve or shield to receive the needle. The use of these devices provides a way to make minimally invasive bone entry into the bony structure of the spine of a surgical patient.

Positioning the needle tip is extremely important and errors in properly doing this can result in serious nerve injury to the patient. To avoid this, the surgeon often relies on x-ray or other imaging techniques to insure the needle tip entry into the bone is proper and avoids cutting into the nerve or spinal cord.

The present invention described below has an improved capacity for imaging the needle tip during the surgical procedure.

SUMMARY OF THE INVENTION

An improved handheld instrument assembly for penetrating into a patient's spine, the instrument assembly has a needle, an outer sleeve, and a removable handle. The needle has a shaft with a bone penetrating tip at a distal end and an enlarged head rotationally fixed to the needle shaft at a proximal end. The outer sleeve is for receiving the needle. The outer sleeve has a length shorter than the needle when the needle tip extends past a distal end of the sleeve and at a proximal end of the sleeve has a handle attachment having a distal side and a proximal side rotationally fixed to the sleeve. The removable handle is configured to removably attach to and engage the handle attachment from the distal side or the proximal side at the discretion of a surgeon. The removable handle has a "T" shaped body. The removable handle has a slotted opening on a frontal side, the slotted opening being sized to pass over the outer sleeve between the distal end and the handle attachment when the needle is inserted into the patient.

The handle attachment has an upper and a lower square or rectangular body portion. The upper portion is above and the lower portion is below a pair of protrusions. Each protrusion has a hole. The "T" shaped body of the removable handle has a pair of pins aligned to engage the pair of holes on the handle attachment and the square or rectangular body portions fit inside the slotted opening on assembly. The attachment portion of the sleeve can have a threaded portion at the proximal end. The treaded portion extends above the "T" shaped body of the handle when assembled. The needle enlarged end is configured to fit onto a top of the threaded portion of the handle attachment. The enlarged end can have grooves or slots extending parallel to an axis of the needle shaft.

The improved handheld instrument assembly further has a handle extension. The handle extension has a cap end with an opening configured to fit over the enlarged end of the needle, and an elongated handle for positioning the surgeon's hand away from the assembly and out of the x-ray field when inserted in the patient to facilitate imaging the needle. The cap can have threads to engage the threads of the handle attachment. On attachment of the handle extension, the "T" shaped handle can be removed to further facilitate imaging. Also, the device can be introduced or otherwise used without the "T" shaped handle.

BRIEF DESCRIPTION OF THE DRAWINGS

The invention will be described by way of example and with reference to the accompanying drawings in which.

DETAILED DESCRIPTION OF THE INVENTION

Figure 1:
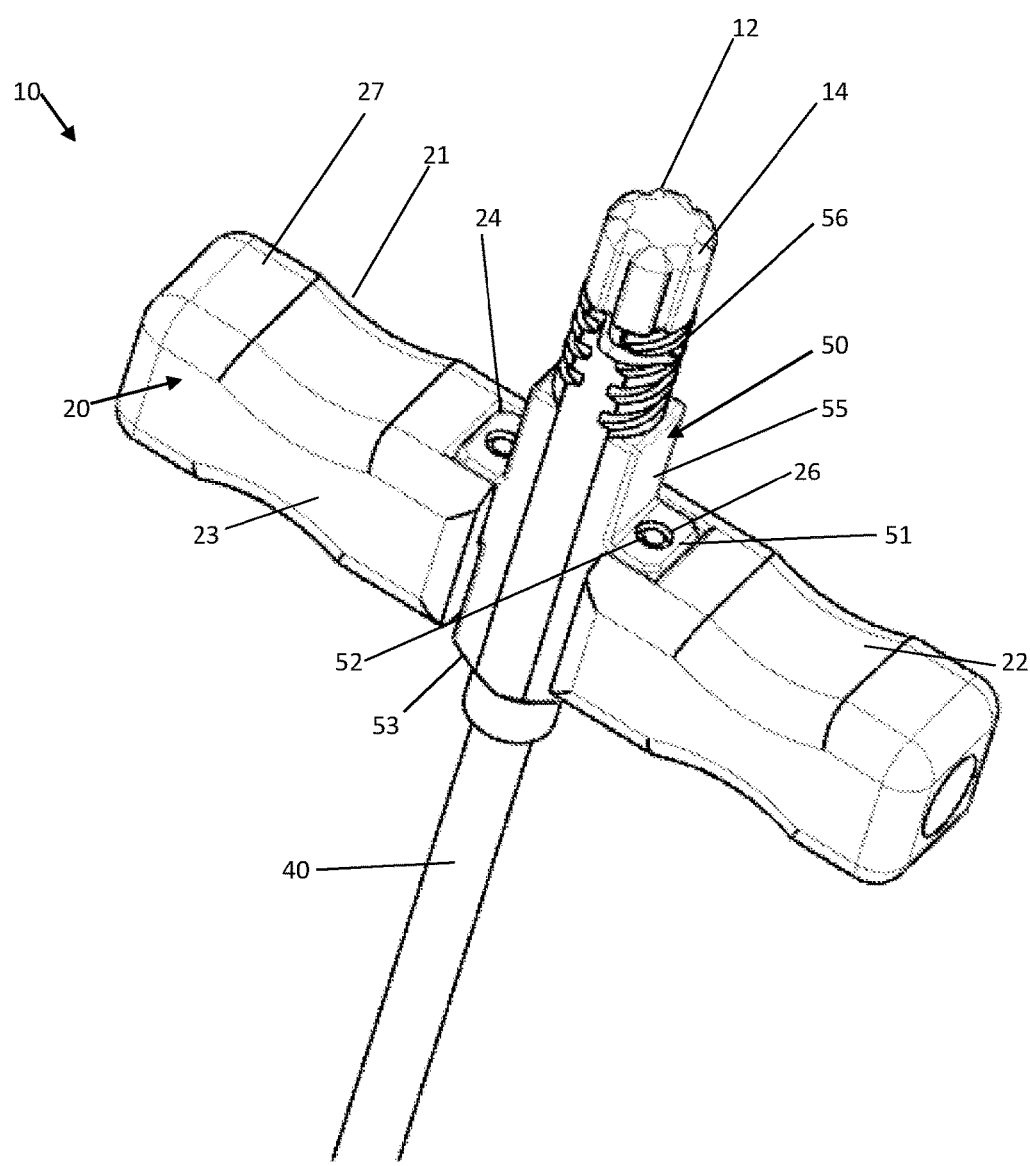
FIG. 1 is a partial perspective view of the present invention showing the removable handle attached from a lower mounting position to the handle attachment.

With reference to FIGS. 1-6 an improved handheld instrument assembly for penetrating into a patient's spine is illustrated. The instrument assembly 10, as illustrated, has a needle 12, an outer sleeve 40, and a removable handle 20. The needle 12 has a shaft 13 with a bone penetrating tip 11 at a distal end and an enlarged head 14 rotationally fixed to the needle shaft 13 at a proximal end. The outer sleeve 40 is for receiving the needle 12. The outer sleeve 40 has a length shorter than the needle 12 wherein the needle tip 11 extends past a distal end 41 of the sleeve 40 and at a proximal end 43 of the sleeve 40 has a handle attachment 50 having a distal side and a proximal side rotationally fixed to the sleeve 40. As shown, at the proximal end 43 of the sleeve 40 is shown a handle attachment 50 having an outer distal portion 53 and a proximal portion 55. The handle attachment 50 is rotationally fixed to the sleeve 40. The removable handle 20 is configured to removably attach to and engage the handle attachment 50 from the distal side or the proximal side at the discretion of a surgeon. The removable handle has a "T" shaped body 22. The removable handle 20 has a slotted opening 24 on a frontal side 23, the slotted opening 24 is sized to pass over the outer sleeve 40 between the distal end and the handle attachment 50 when the needle 12 is inserted into the patient.

Figure 2:
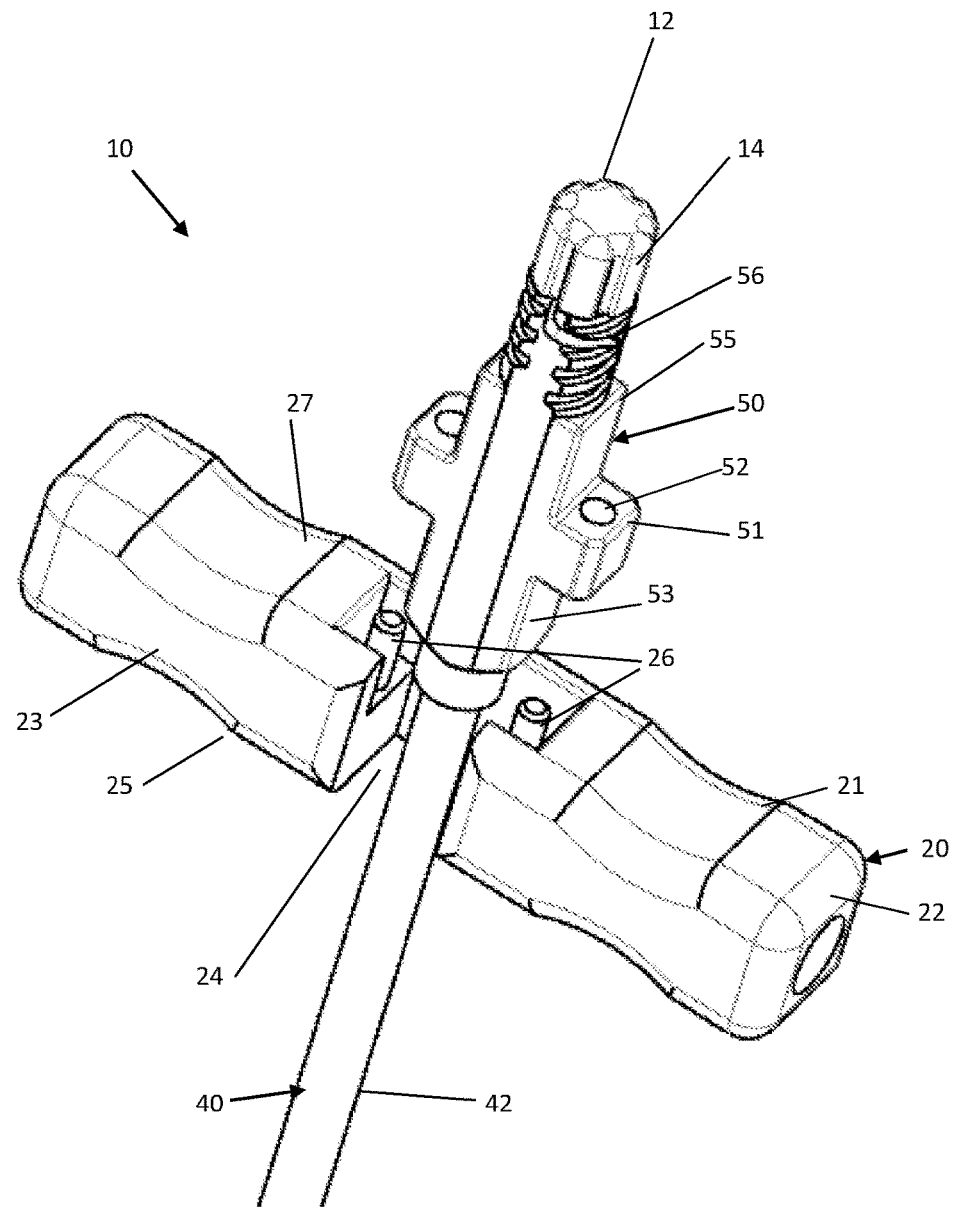
FIG. 2 is an exploded view of the upper perspective view of FIG. 1 showing the removable handle prior to being attached from its lower position.

With reference to FIGS. 1 and 2, the handle 20 is shown being attached from a lower portion of the instrument 10. In doing so, the slotted opening 24 allows the sleeve 40 to slip into the slotted opening 24, and thereafter the handle 20 can be pulled upward into engagement with the handle attachment portion 50, as illustrated. When this occurs, the pins 26 will align with the holes 52 and engage them as the protrusions 51 slide into the openings or concavity 28 in the handle body 22. On assembly, as shown in FIG. 1, the handle 20 is nicely positioned attached from a lower location into the attachment, at this point the lower distal end portion 53 and protrusions 51 of the attachment 50 are fully seated into the removable handle 20 as the protrusions 51 are resting inside the concavity 28 provided in the handle body 22. The handle 20, when turned in this configuration, has one side 25 located closer to the distal side and the upper open side 27 facing toward the proximal side. A rear side 21 and a front face or side 23 are illustrated extending between the sides 25 and 27.

Figure 3:
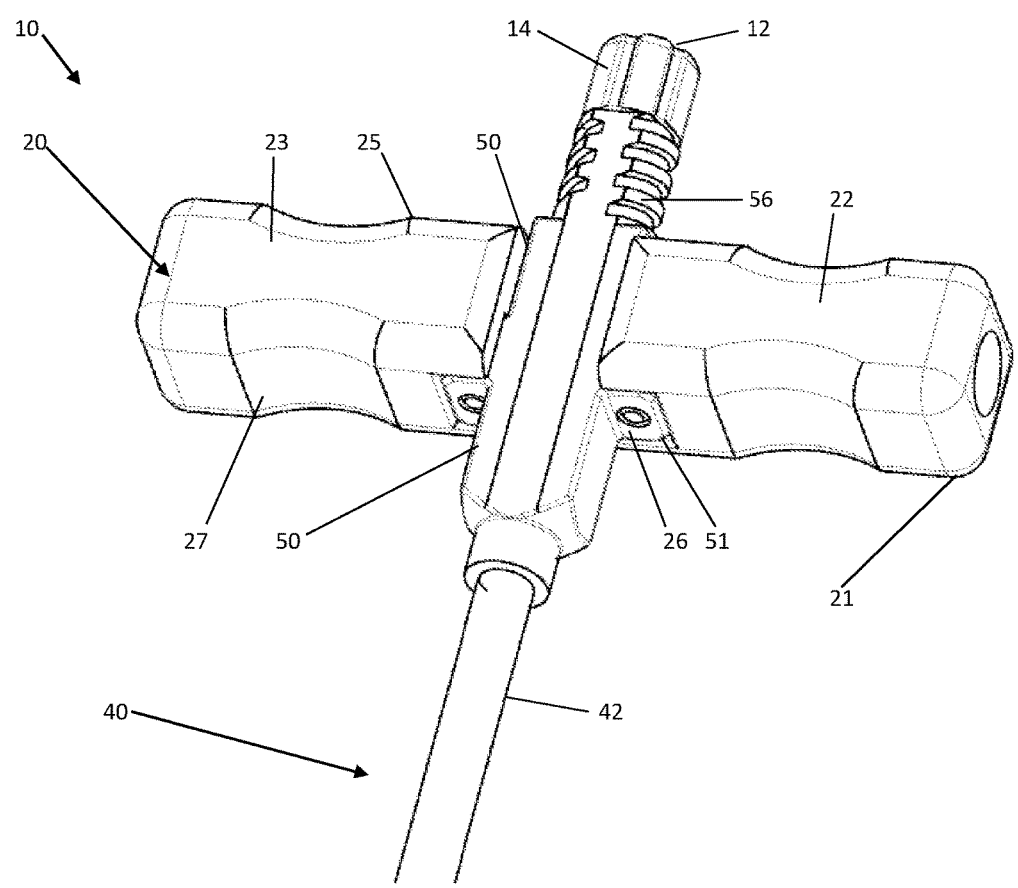
FIG. 3 illustrates a partial perspective view of the device of the present invention with the removable handle shown attached to the upper portion of the handle attachment.
Figure 4:
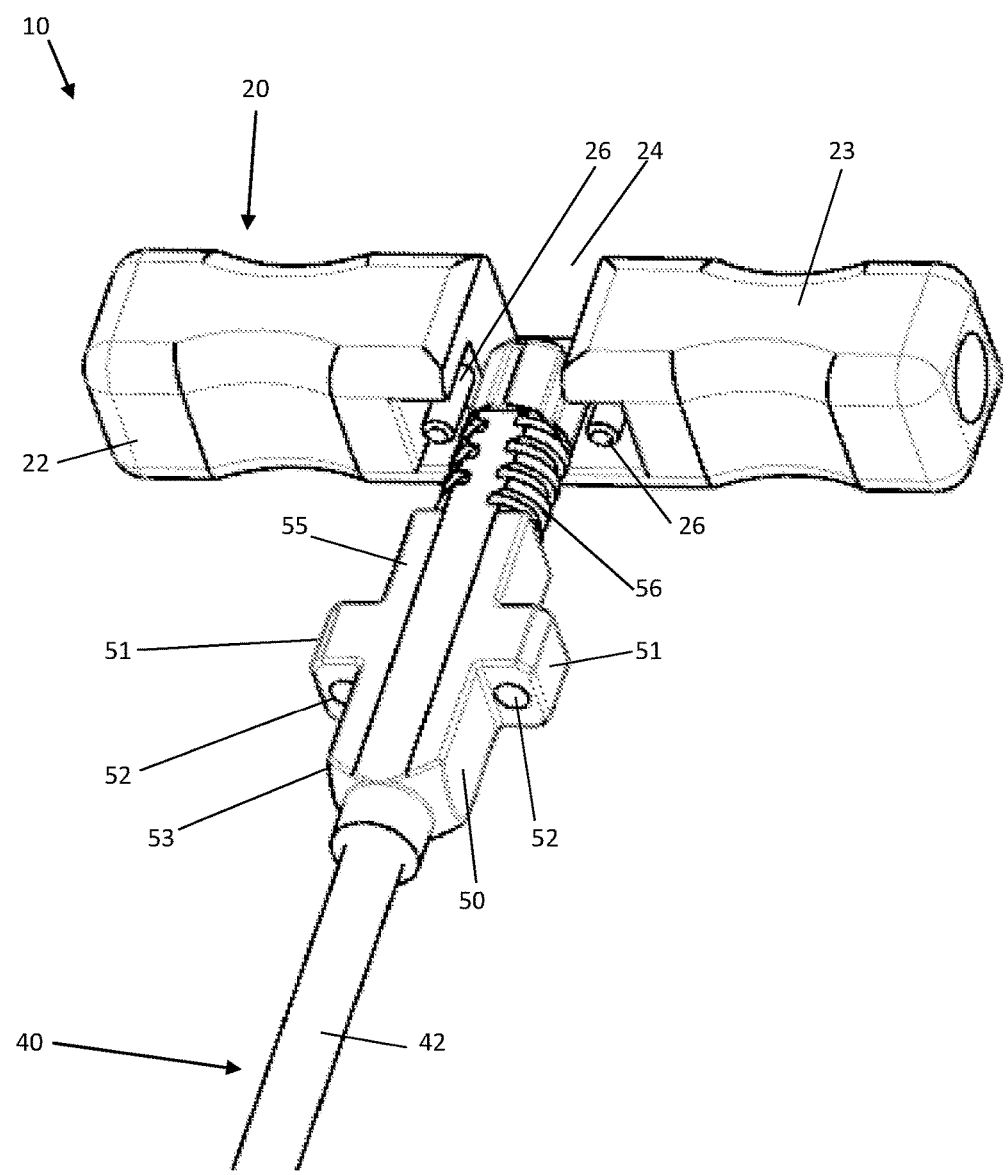
FIG. 4 shows a perspective view taken from FIG. 3 with the handle prior to being attached to the upper portion of the handle attachment.

With reference to FIGS. 3 and 4, a similar perspective view is shown, however, in this occurrence the handle 20 is shown mounted to the upper portion 55 of the handle attachment 50. In this case, the pins 26 will come from the proximal end towards the distal end and the handle assembly 20 will lock securely on that portion of the handle attachment 50. As illustrated, the handle attachment 50 has basically a symmetrical such that the handle 20 can be mounted from either an upper location or a lower location.

Figure 5:
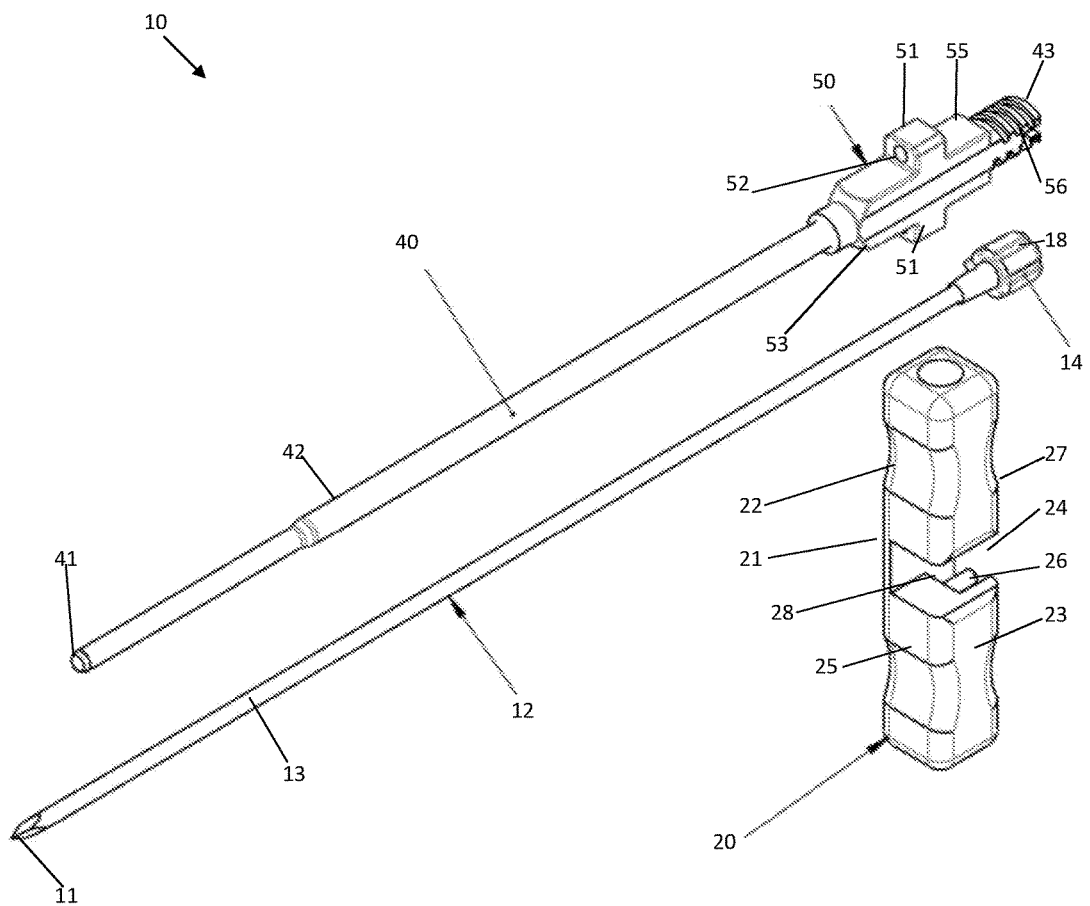
FIG. 5 is a perspective exploded view of the device of the present invention showing the needle, the outer sleeve and the removable handle.

FIG. 5 shows an exploded view of the needle 12, the outer sleeve 40 and the removable handle 20.

Figure 6:
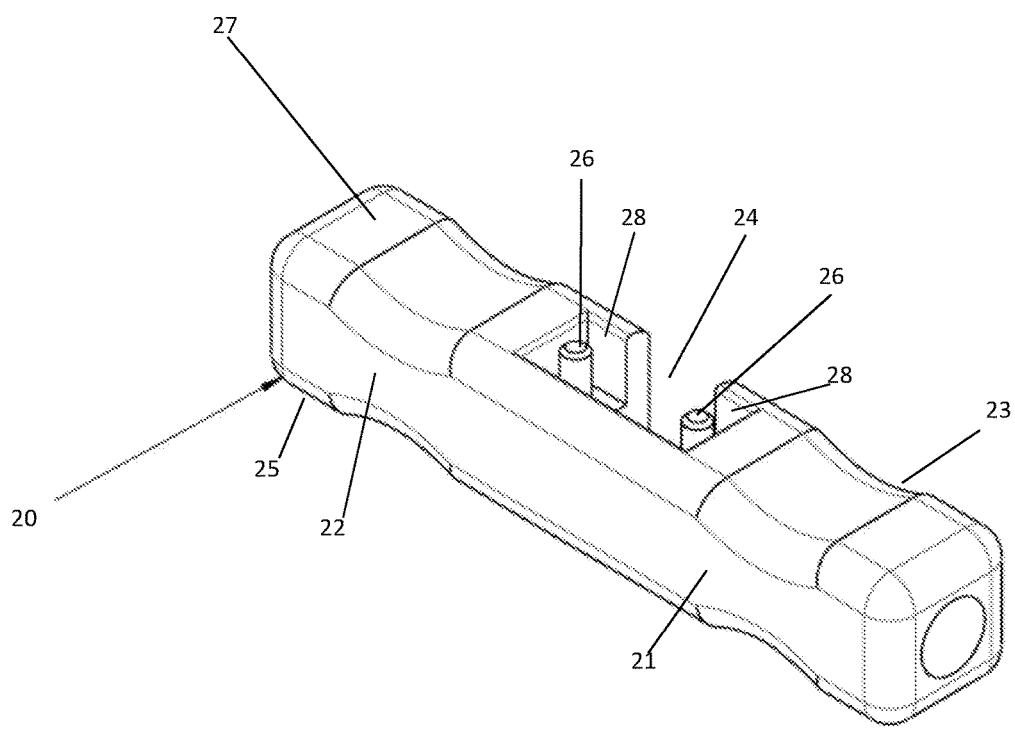
FIG. 6 is a perspective view of the removable handle made according to the present invention.

The handle attachment 50 at the distal end has the lower distal portion 53 with a square or rectangular body portion and at the proximal end has the proximal portion 55 with a lower square or rectangular body portion. Between the upper and lower portions is a pair of protrusions 51. Each protrusion 51 has a hole 52. As shown in FIG. 6, the "T" shaped body 22 of the removable handle 20 has a pair of pins 26 aligned to engage the pair of holes 52 on the handle attachment 50 and the square or rectangular body portions 53, 55 fit inside enlarged center concavity 28 adjacent the slotted opening 24 on assembly. The handle attachment 50 of the sleeve 40 can have a threaded portion 56 at the proximal end 43. The treaded portion 56 extends above the "T" shaped body 22 of the handle 20 when assembled. The needle 12 enlarged end 14 is configured to fit onto a top proximal end of the threaded portion 56 of the handle attachment 50. The enlarged end 14 of the needle 12 can have grooves or slots 18 extending parallel to an axis of the needle shaft 13.

Figure 7:
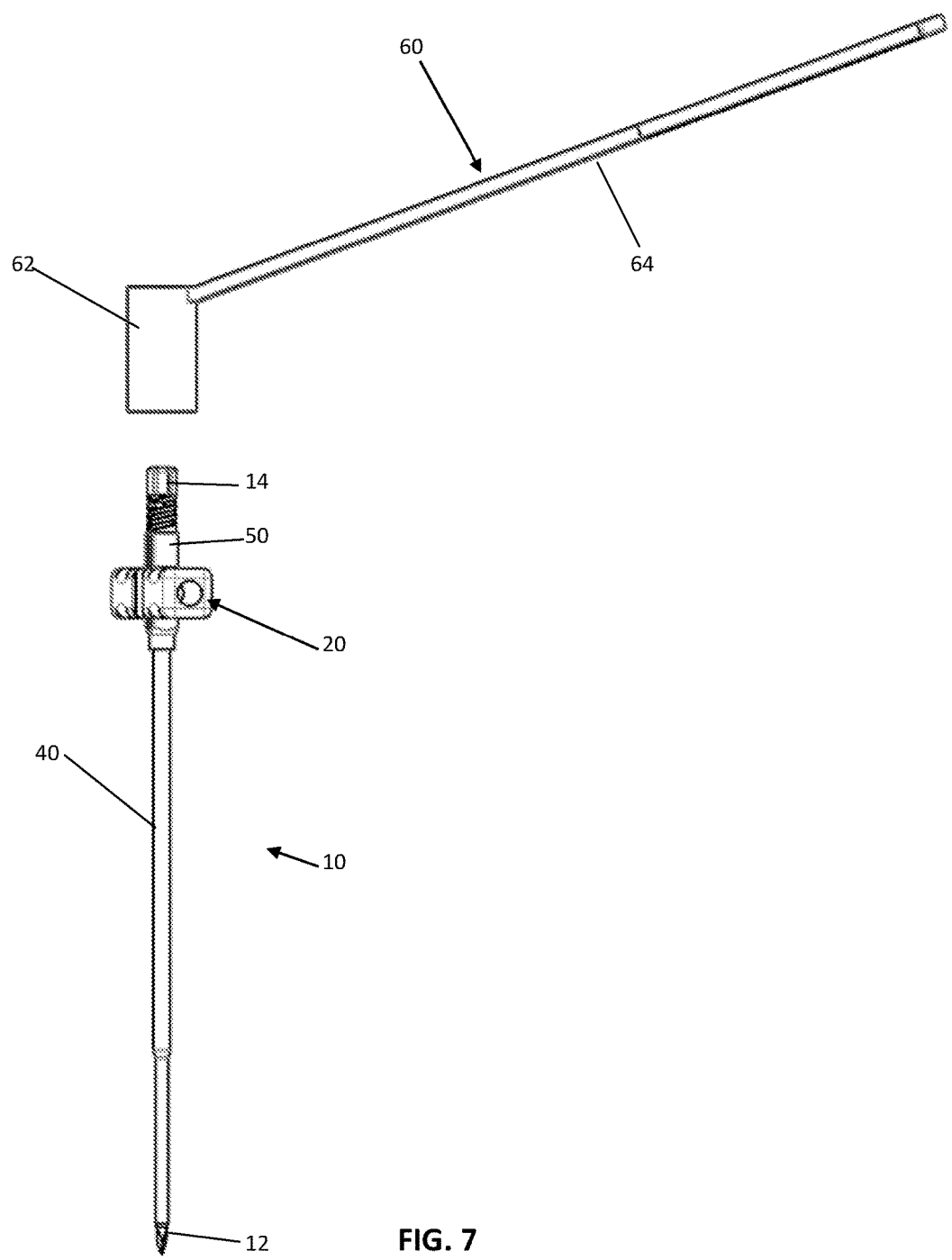
FIG. 7 is a plan view of the device of the present invention with a handle extension shown above the device.
Figure 8:
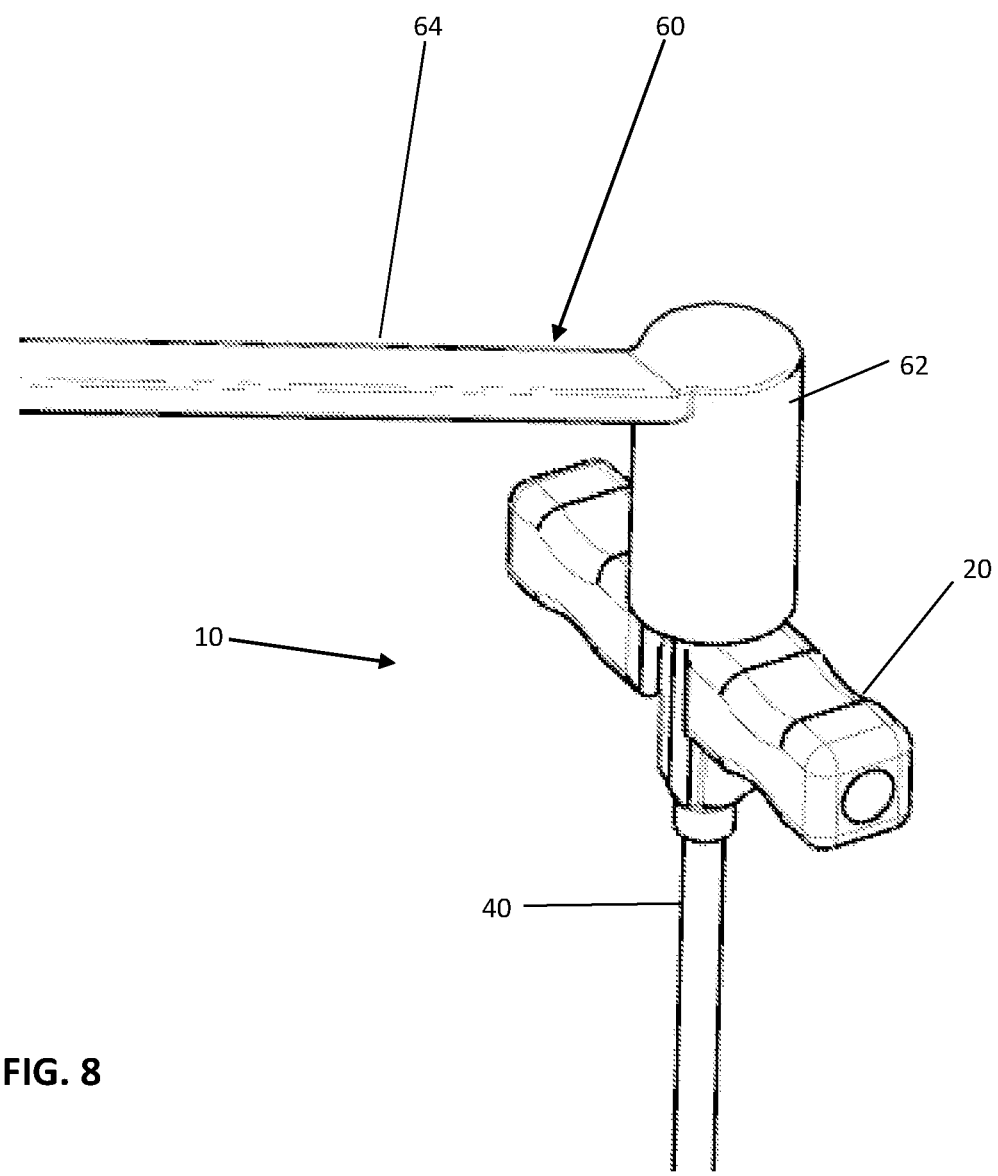
FIG. 8 is a perspective view of the handle extension shown attached at the proximal end of the device made according to the present invention.

With reference to FIGS. 7 and 8, the improved handheld instrument assembly 10 can further be provided with a handle extension 60. The handle extension 60 has a cap end 62 with an opening configured to fit over the enlarged end 14 of the needle 12 and optionally engage the threaded portion 56 of the handle attachment 50 and/or the proximal portion 55. The handle extension 60 further has an elongated handle 64 that enables the surgeon to position his hand away from the assembly 10 when the needle 12 is inserted in the patient. This facilitates imaging the needle 12 and bone penetrating tip end portion of the needle shaft 13 in the patient using x-ray or other imaging equipment. By having the hand removed from the location of the instrument assembly 10, the view or x-ray can be less obstructed than if the surgeon had his hand in the way. This enables the surgeon to direct the angulation of the entire instrument 10 using the handheld extension 60. When the extension 60 is attached to the instrument 10 it is possible to further remove the "T" shaped handle body 22 to further facilitate imaging. The cap 62 can have threads to engage the threads 56 of the handle attachment 50.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An improved handheld instrument assembly for penetrating into a patient's spine, the instrument assembly comprises:
   a needle having a shaft with a bone penetrating tip at a distal end and an enlarged head rotationally fixed to the needle shaft at a proximal end, wherein the enlarged head has grooves or slots extending parallel to an axis of the needle shaft;
   an outer sleeve for receiving the needle, the outer sleeve having a length shorter than the needle so that the needle tip extends past a distal end of the sleeve and a proximal end of the sleeve has a handle attachment having a distal side and a proximal side rotationally fixed to the sleeve and wherein the handle attachment has an upper and a lower square or rectangular body portion, the upper portion being above and the lower portion being below a pair of protrusions, each protrusion having a hole;
   a removable handle, the removable handle configured to removably attach to and engage the handle attachment from the distal side or the proximal side at the discretion of a surgeon wherein the removable handle has a "T" shaped body, the "T" shaped body of the removable handle has a pair of pins aligned to engage the pair of holes on attachment and the square or rectangular body portions fit inside a slotted opening on assembly, wherein the removable handle is configured to be attached from a lower portion of the instrument as the slotted opening allows the outer sleeve to slip into the slotted opening and thereafter the removable handle can be pulled upward into engagement with the handle attachment and the pins align and engage with the holes as the protrusions enter an opening or concavity in the "T" shaped body, additionally, the removable handle is further configured to be attached from an upper portion of the instrument by lowering the removable handle from the proximal side of the handle attachment toward the distal side as the pins move into the holes from the proximal end toward the distal end to secure the removable handle to the handle attachment, and wherein the handle attachment of the outer sleeve has a threaded portion at the proximal end, the threaded portion extending above the "T" shaped body when assembled wherein the needle enlarged head is configured to fit onto a top of the threaded portion of the handle attachment, and the removable handle is configured to pass over the needle enlarged head when attached from the upper portion of the instrument, and wherein the removable handle has the slotted opening on a frontal side, the slotted opening being sized to pass over the outer sleeve between the distal end and the handle attachment when the needle is inserted into the patient; and
   a handle extension, the handle extension having a cap end with an opening configured to fit over the enlarged head of the needle, and an elongated handle for positioning a surgeon's hand away from the assembly when inserted in the patient to facilitate imaging the needle and wherein the cap end engages the upper square or upper rectangular body portion at a proximal portion of the handle attachment, wherein when the handle extension is attached to the instrument assembly, the "T" shaped body can be removed to further facilitate imaging.

* * * * *